US011504097B2

(12) United States Patent
Dickie et al.

(10) Patent No.: US 11,504,097 B2
(45) Date of Patent: Nov. 22, 2022

(54) SYSTEMS AND METHODS FOR ACQUIRING RAW ULTRASOUND DATA FROM AN ULTRASOUND MACHINE USING A WIRELESSLY CONNECTED DEVICE

(71) Applicant: Clarius Mobile Health Corp., Burnaby (CA)

(72) Inventors: Kris Dickie, Vancouver (CA); Nishant Uniyal, Vancouver (CA); Benjamin Eric Kerby, Richmond (CA)

(73) Assignee: Clarius Mobile Health Corp., Vancouver (CA)

( * ) Notice: Subject to any disclaimer, the term of this patent is extended or adjusted under 35 U.S.C. 154(b) by 1140 days.

(21) Appl. No.: 15/694,061

(22) Filed: Sep. 1, 2017

(65) Prior Publication Data

US 2019/0069884 A1 Mar. 7, 2019

(51) Int. Cl.
*A61B 8/00* (2006.01)
*A61B 8/08* (2006.01)
*A61B 8/14* (2006.01)

(52) U.S. Cl.
CPC ............ *A61B 8/56* (2013.01); *A61B 8/14* (2013.01); *A61B 8/4411* (2013.01); *A61B 8/4427* (2013.01); *A61B 8/4483* (2013.01); *A61B 8/461* (2013.01); *A61B 8/468* (2013.01); *A61B 8/5207* (2013.01); *A61B 8/565* (2013.01)

(58) Field of Classification Search
CPC ......... A61B 8/56; A61B 8/468; A61B 8/4411; A61B 8/4427; A61B 8/565; A61B 8/5207; A61B 8/14; A61B 8/4483; A61B 8/461
See application file for complete search history.

(56) References Cited

U.S. PATENT DOCUMENTS

| | | | |
|---|---|---|---|
| 5,920,317 A | 7/1999 | McDonald | |
| 6,171,244 B1 | 1/2001 | Finger et al. | |
| 6,263,094 B1 | 7/2001 | Rosich et al. | |
| 6,780,154 B2 | 8/2004 | Hunt et al. | |
| 7,189,205 B2 | 3/2007 | McMorrow et al. | |

(Continued)

OTHER PUBLICATIONS

Lee, H. J. et al., "The Effect of Wireless LAN-Based PACS Device for Portable Imaging Modalities", in Journal of Digital Imaging 23.2 (2010): 185-191.

(Continued)

*Primary Examiner* — Keith M Raymond
*Assistant Examiner* — Milton Truong
(74) *Attorney, Agent, or Firm* — Julian Ho; Susan Ben-Oliel

(57) ABSTRACT

The present embodiments relate generally to systems and methods for acquiring raw ultrasound data from an ultrasound machine using a wirelessly connected device. The systems can be configured to display ultrasound images on a display device and receive input to select the ultrasound images for which to retrieve corresponding raw ultrasound data from the ultrasound machine. A raw data buffer provided at the ultrasound machine may be capable of storing a first time duration of raw ultrasound data. An image display buffer provided at the wireless device may store: processed ultrasound image data corresponding to the raw ultrasound data stored in the raw data buffer; and previously-received processed ultrasound image data that has no corresponding raw ultrasound data stored in the raw data buffer.

20 Claims, 9 Drawing Sheets

(56) References Cited

U.S. PATENT DOCUMENTS

| | | |
|---|---|---|
| 8,073,211 B2 | 12/2011 | Halmann |
| 8,490,489 B2 | 7/2013 | Randall et al. |
| 8,491,479 B2 | 7/2013 | Pelissier et al. |
| 8,500,645 B2 | 8/2013 | Cohen et al. |
| 2003/0139664 A1 | 7/2003 | Hunt et al. |
| 2003/0139671 A1 | 7/2003 | Walston et al. |
| 2004/0077952 A1 | 4/2004 | Rafter et al. |
| 2004/0133105 A1* | 7/2004 | Ostrovsky ........... G01S 15/8936 600/437 |
| 2005/0049500 A1* | 3/2005 | Babu ................ A61B 8/13 600/443 |
| 2007/0161898 A1 | 7/2007 | Hao et al. |
| 2007/0232915 A1 | 10/2007 | Pelissier et al. |
| 2008/0114253 A1 | 5/2008 | Randall et al. |
| 2008/0205715 A1 | 8/2008 | Halmann |
| 2009/0203996 A1* | 8/2009 | Thiele ................ A61B 8/467 600/441 |
| 2011/0034209 A1 | 2/2011 | Rubinsky et al. |
| 2011/0055148 A1* | 3/2011 | Berg ................ G16H 30/20 707/602 |
| 2012/0004545 A1 | 1/2012 | Ziv-Ari et al. |
| 2012/0010507 A1 | 1/2012 | Sanders |
| 2014/0058266 A1* | 2/2014 | Call .................. G01S 7/52098 600/448 |
| 2016/0173770 A1* | 6/2016 | Fosodeder .......... G01S 7/52098 348/77 |
| 2017/0086798 A1 | 3/2017 | Bjaerum et al. |

OTHER PUBLICATIONS

Abstract of Boni, E. et al., "Multi-channel Raw-Data Acquisition for Ultrasound Research", in 2014 17th Euromicro Conference on Digital System Design (DSD), IEEE, Aug. 27-29, 2014, available at http://ieeexplore.ieee.org/document/6927304/?part=1, last accessed Sep. 19, 2017.

* cited by examiner

SYSTEMS AND METHODS FOR ACQUIRING RAW ULTRASOUND DATA FROM AN ULTRASOUND MACHINE USING A WIRELESSLY CONNECTED DEVICE

FIELD

This invention generally relates to ultrasound imaging systems, and in particular, systems and methods for acquiring raw ultrasound data from an ultrasound machine using a wirelessly connected device.

BACKGROUND

Ultrasound imaging systems are a powerful tool for performing real-time, non-invasive imaging procedures in a wide range of medical applications. An ultrasound machine typically includes a transducer which sends out ultrasound signals into a target object. Ultrasound waves are reflected back from the target object and are received by the transducer. The received data is then subject to a number of processing steps to generate an ultrasound image of the target object.

As the raw received data is processed, a portion of the information contained in the raw data is lost as the size is reduced. Having access to this raw data may be useful for a number of reasons, including performing advanced analyses and research. Some ultrasound systems have specialized hardware to allow access to the raw data.

Some newer ultrasound machines include a wirelessly connected transducer that provides advantages over traditional corded ultrasound machines, including improved portability and ergonomics. Current wireless communication protocols such as Wi-Fi™ may not have the bandwidth required to stream both the images and raw data in real-time.

There is thus a need for improved ultrasound systems and methods that enable raw ultrasound data to be stored and transmitted from a wireless probe. The embodiments discussed herein may address and/or ameliorate at least some of the aforementioned drawbacks identified above. The foregoing examples of the related art and limitations related thereto are intended to be illustrative and not exclusive. Other limitations of the related art will become apparent to those of skill in the art upon a reading of the specification and a study of the drawings herein.

BRIEF DESCRIPTION OF THE DRAWINGS

Non-limiting examples of various embodiments of the present disclosure will next be described in relation to the drawings, in which.

DETAILED DESCRIPTION

Figure 1:
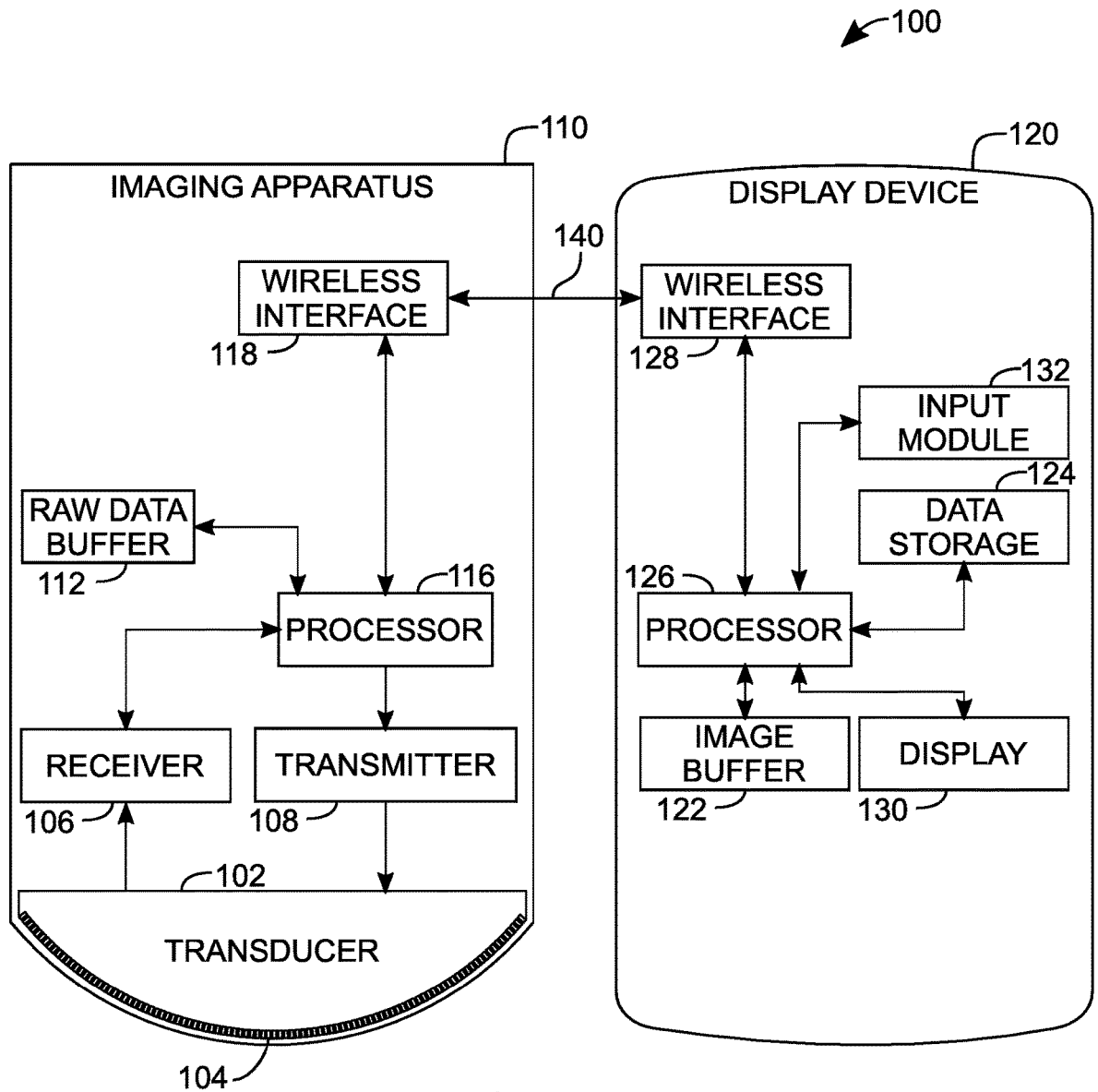
FIG. 1 is a functional block diagram of an ultrasound system, in accordance with at least one embodiment of the present invention.

In a first broad aspect of the present disclosure, there is provided a method for acquiring raw ultrasound data from an ultrasound machine using a wirelessly connected device, the method involving, at the wirelessly connected device: receiving processed ultrasound image data from the ultrasound machine, wherein the received processed ultrasound image data corresponds to raw ultrasound data stored in a raw data buffer at the ultrasound machine, wherein the raw data buffer is capable of storing a first time duration of raw ultrasound data, and the received processed ultrasound image data requires less storage capacity than the corresponding raw ultrasound data stored in the raw data buffer; storing the processed ultrasound image data in an image display buffer, the image display buffer being capable of storing a second time duration of processed ultrasound image data longer than the first time duration, and wherein the image display buffer simultaneously stores: (i) the received processed ultrasound image data corresponding to the raw ultrasound data stored in the raw data buffer, and (ii) previously-received processed ultrasound image data that has no corresponding raw ultrasound data stored in the raw data buffer; receiving input selecting one or more images of the received processed ultrasound image data stored in the image display buffer; transmitting information identifying the selected one or more images to the ultrasound machine, wherein the ultrasound machine identifies the raw ultrasound data, stored in the raw data buffer, that corresponds to the selected one or more images, for return to the wirelessly connected device; and receiving the identified raw ultrasound data corresponding to the selected one or more images.

In some embodiments, both (i) the received processed ultrasound image data corresponding to the raw ultrasound data stored in the raw data buffer at the ultrasound machine and (ii) the previously-received processed ultrasound image data stored in the image display buffer are viewable in a user interface of the wirelessly connected device that navigates images stored in the image display buffer.

In some embodiments, prior to receiving input selecting the one or more images, the user interface is configured to display an image of the received processed ultrasound image data, and the user interface indicates that corresponding raw ultrasound data is available to be retrieved from the ultrasound machine.

In some embodiments, prior to receiving input selecting the one or more images, the user interface is configured to display an image from the previously-received processed ultrasound image data, and the user interface does not indicate that corresponding raw ultrasound data is available to be retrieved from the ultrasound machine.

In some embodiments, the method further involves storing the received raw ultrasound data, corresponding to the selected one or more images, in a storage location different from the image display buffer.

In some embodiments, prior to receiving the processed ultrasound image data, the method further involves: receiving input indicating a raw ultrasound data collection mode of the ultrasound machine is to be activated; and directing the ultrasound machine to activate the raw ultrasound data collection mode.

In some embodiment, prior to receiving the input indicating the raw ultrasound data collection mode is to be activated, the method further involves: operating in an imaging mode where the previously-received processed ultrasound image data is received, and no corresponding raw ultrasound data is stored in the raw data buffer at the ultrasound machine.

In some embodiments, prior to receiving the input indicating the raw ultrasound data collection mode of the ultrasound machine is to be activated, the method further involves: receiving an ultrasound image feed including the previously-received processed ultrasound image data; and displaying the ultrasound image feed; and wherein during receipt of the input indicating the raw ultrasound data collection mode at the ultrasound machine is to be activated, the method further involves continuing to receive and display the ultrasound image feed, the ultrasound image feed including the received processed ultrasound image data.

In some embodiments, the ultrasound image feed is continued to be received and displayed when the raw ultrasound data collection mode is activated without substantial delay in displaying successive frames of the ultrasound image feed.

In some embodiments, after the received processed ultrasound image data is stored in the image display buffer, the method further involves: receiving input indicating the raw ultrasound data collection mode of the ultrasound machine is to be deactivated; and directing the ultrasound machine to deactivate the raw ultrasound data collection mode.

In some embodiments, the input indicating the raw ultrasound data collection mode of the ultrasound machine is to be activated involves pressing of a button on a user interface provided on one of the ultrasound machine and the wirelessly connected device, and the received input indicating the raw ultrasound data collection mode of the ultrasound machine is to be deactivated involves a release of the button.

In some embodiments, prior to receiving the input selecting one or more images from the received processed ultrasound image data stored in the image display buffer, the method further involves: receiving input to stop ultrasound data acquisition at the ultrasound machine; and directing the ultrasound machine to stop ultrasound data acquisition.

In another broad aspect of the present disclosure, there is provided a method for transmitting raw ultrasound data from an ultrasound machine to a wirelessly connected device, the method including, at the ultrasound machine: acquiring raw ultrasound data; storing the acquired raw ultrasound data in a raw data buffer, wherein the raw data buffer is capable of storing a first time duration of raw ultrasound data; generating processed ultrasound image data from the raw ultrasound data, the processed ultrasound image data requiring less storage capacity than the acquired raw ultrasound data; transmitting the processed ultrasound image data to the wirelessly connected device, wherein the transmitted processed ultrasound image data is stored at the wirelessly connected device in an image display buffer, the image display buffer being capable of storing a second time duration of processed ultrasound image data longer than the first time duration, and wherein the image display buffer simultaneously stores: (i) the transmitted processed ultrasound image data corresponding to the raw ultrasound data stored in the raw data buffer, and (ii) previously-transmitted processed ultrasound image data that has no corresponding raw ultrasound data stored in the raw data buffer; receiving, from the wirelessly connected device, information identifying one or more images selected from the transmitted processed ultrasound image data; identifying the raw ultrasound data, stored in the raw data buffer, corresponding to the one or more images; and transmitting, to the wirelessly connected device, the raw ultrasound data, stored in the raw data buffer, corresponding to the one or more images.

In some embodiments, prior to storing the acquired raw ultrasound data in the raw data buffer, the method further involves: receiving direction from the wirelessly connected device that a raw ultrasound data collection mode of the ultrasound machine is to be activated; and activating the raw ultrasound data collection mode.

In some embodiments, prior to receiving the direction from the wirelessly connected device that the raw ultrasound data collection mode is to be activated, the method further involves: operating in an imaging mode where the previously-transmitted processed ultrasound image data is generated, and no corresponding raw ultrasound data is stored in the raw data buffer.

In some embodiments, prior to receiving the direction from the wirelessly connected device that the raw ultrasound data collection mode is to be activated, the method further involves: generating an ultrasound image feed including the previously-transmitted processed ultrasound image data; and transmitting the ultrasound image feed to the wirelessly connected device; and wherein upon receipt of the direction from the wirelessly connected device that the raw ultrasound data collection mode is to be activated, the method further involves: continuing to generate and transmit the ultrasound image feed, the ultrasound image feed comprising the transmitted processed ultrasound image data.

In some embodiments, the ultrasound image feed is continued to be generated and transmitted without substantial delay in transmitting successive frames of the ultrasound image feed to the wirelessly connected device.

In some embodiments, after transmitting the processed ultrasound image data to the wirelessly connected device, the method further involves: receiving direction from the wirelessly connected device to deactivate the raw ultrasound data collection mode; and deactivating the raw ultrasound data collection mode, such that additional raw ultrasound data is acquired for generation of additional processed ultrasound image data, without storage of the additional raw ultrasound data in the raw data buffer.

In some embodiments, the input indicating the raw ultrasound data collection mode of the ultrasound machine is to be activated includes pressing of a button on a user interface provided on one of the ultrasound machine and the wirelessly connected device, and the received input indicating the raw ultrasound data collection mode of the ultrasound machine is to be deactivated includes a release of the button.

In another broad aspect of the present disclosure, there is provided a system for providing raw ultrasound data. The system includes an ultrasound machine configured to: acquire raw ultrasound data; store the acquired raw ultrasound data in a raw data buffer, wherein the raw data buffer is capable of storing a first time duration of raw ultrasound data; generate processed ultrasound image data from the raw ultrasound data, the processed ultrasound image data requiring less storage capacity than the acquired raw ultrasound data; and transmit the processed ultrasound image data; and a wirelessly connected device configured to: receive processed ultrasound image data from the ultrasound machine, store the processed ultrasound image data in an image display buffer, the image display buffer being capable of storing a second time duration of processed ultrasound image data longer than the first time duration, and wherein the image display buffer simultaneously stores: (i) the received processed ultrasound image data corresponding to the raw ultrasound data stored in the raw data buffer, and (ii) processed ultrasound image data, previously-received at the wirelessly connected device, that has no corresponding raw ultrasound data stored in the raw data buffer; receive input selecting one or more images of the received processed ultrasound image data stored in the image display buffer; and transmit information identifying the selected one or more images to the ultrasound machine; wherein the ultrasound machine is further configured to: identify the raw ultrasound data, stored in the raw data buffer, corresponding to the selected one or more images; and transmit, to the wirelessly connected device, the raw ultrasound data, stored in the raw data buffer, corresponding to the selected one or more images.

For simplicity and clarity of illustration, where considered appropriate, reference numerals may be repeated among the figures to indicate corresponding or analogous elements or steps. In addition, numerous specific details are set forth in order to provide a thorough understanding of the exemplary embodiments described herein. However, it will be understood by those of ordinary skill in the art that the embodiments described herein may be practiced without these specific details. In other instances, certain steps, signals, protocols, software, hardware, networking infrastructure, circuits, structures, techniques, well-known methods, procedures and components have not been described or shown in detail in order not to obscure the embodiments generally described herein.

Furthermore, this description is not to be considered as limiting the scope of the embodiments described herein in any way. It should be understood that the detailed description, while indicating specific embodiments, are given by way of illustration only, since various changes and modifications within the scope of the disclosure will become apparent to those skilled in the art from this detailed description. Accordingly, the specification and drawings are to be regarded in an illustrative, rather than a restrictive, sense.

Referring to FIG. 1, shown there generally as 100 is an example of an ultrasound system according to at least one embodiment of the present invention. Ultrasound system 100 may be operable to transmit ultrasound energy to a target object, receive ultrasound energy reflected from the target object and generate ultrasound image data based on the reflected ultrasound energy. The ultrasound system 100 may include an ultrasound imaging apparatus 110 communicatively connected with a multi-use electronic display device 120. A wireless connection 140 may connect ultrasound imaging apparatus 110 with display device 120 to permit the transmission of data and commands between the two.

Ultrasound imaging apparatus 110 may include, for example, a transducer array 102 with a plurality of transducer elements 104, a transmitter 108, a receiver 106, a processor 116, raw data buffer 112, and a wireless interface 118. The imaging apparatus 110 may also generally be referred to as an ultrasound machine, probe, imaging device, and/or scanner herein.

Transducer elements 104 are operable to both emit and receive ultrasound energy. When energized by a transmitter 108, the transducer elements 104 produce a burst of ultrasound energy. The ultrasound energy produced by transducer array 102 is directed toward a target object. Some of the ultrasound energy is reflected back to transducer array 102 as echo signals. The transducer elements 104 convert the received ultrasound energy into analog electrical signals which are then sent to receiver 106. Receiver 106 may include various well-known elements for digitizing the received ultrasound energy. The raw digitized ultrasound energy may then be transmitted to processor 116 for various processing steps and/or to be stored in raw data buffer 112.

Processor 116 may be configured to apply various processing steps to the raw ultrasound data. These processing steps may be implemented in software or hardware. The processing steps may include one or more of the following: beamforming, summing, in-phase and quadrature, envelope detection and/or compression. Processor 116 may also be configured to store raw or partially processed ultrasound data in raw data buffer 112.

Raw data buffer 112 may be configured to store raw or partially processed ultrasound data. In various embodiments, raw data buffer 112 may be configured as a circular buffer.

Processed ultrasound image data may be provided to wireless interface 118 for transmission to a connected device such as multi-use electronic display device 120 (which, for ease of reference may be referred to simply as "display device" herein). The wireless connection 140 formed between wireless interface 118 and wireless interface 128 may be any conventionally known or future developed wireless communication protocol, such as WiFi™ or WiFi Direct™.

Display device 120 may be a smartphone, table computer, or other suitable display device. Display device 120 may include a display 130, user input module 132, image buffer 122, processor 126, storage device 124, and wireless interface 128. Processed ultrasound image data is received by wireless interface 128 and provided to processor 126. The processed ultrasound image data may be further processed and stored in image buffer 122 and/or displayed on display 130. Input module 132 may receive input (e.g., from a user) to control the operation of imaging apparatus 110. For example, input may be received through input module 132 to request imaging apparatus 110 to transmit raw ultrasound data from imaging apparatus 110. The received raw ultrasound data may then be stored in data storage 124.

In various embodiments, input module 132 may include a touchscreen, a keyboard, a mouse, a voice-activated interface, or other user-machine interfaces now known or later developed.

Raw ultrasound data may include different types of data. For example, the raw ultrasound data may include digitized acoustic signals from individual channels, which is commonly referred to as channel domain or (pre-beamformed) radio frequency (RF) data. The raw ultrasound data may additionally or alternatively include beamformed radio frequency data. Alternatively, or in addition, the raw ultrasound data may include in-phase and quadrature (IQ) data.

Processed ultrasound data may include identifying information that may be used to identify the corresponding raw data. For example, the identifying information may include a frame number, a time stamp, or a universally unique identification number.

Processor 126 may perform one or more processing steps on the processed ultrasound image data to generate an ultrasound image. For example, processor 126 may be operable to combine one or more of the frames generated from the ultrasound image data and/or perform scan conversion.

Data storage 124 can include any one or a combination of volatile memory elements (e.g., random access memory (RAM), such as DRAM, SRAM, etc.) and non-volatile memory elements.

In various embodiments, the display device 120 may receive input to select images of the processed image data for which to retrieve corresponding raw data available on the imaging apparatus 110. As discussed below, this selection may be performed in different ways. For example, the selection methods may include prospective sampling, or retrospective selection of previously acquired image frames stored in an ultrasound image buffer, and/or in substantially real-time while the images are being transmitted from the imaging apparatus 110 and displayed at the display device 120. Several methods are described below with reference to FIG. 2, FIG. 3, FIG. 6, and FIG. 8.

Figure 2:
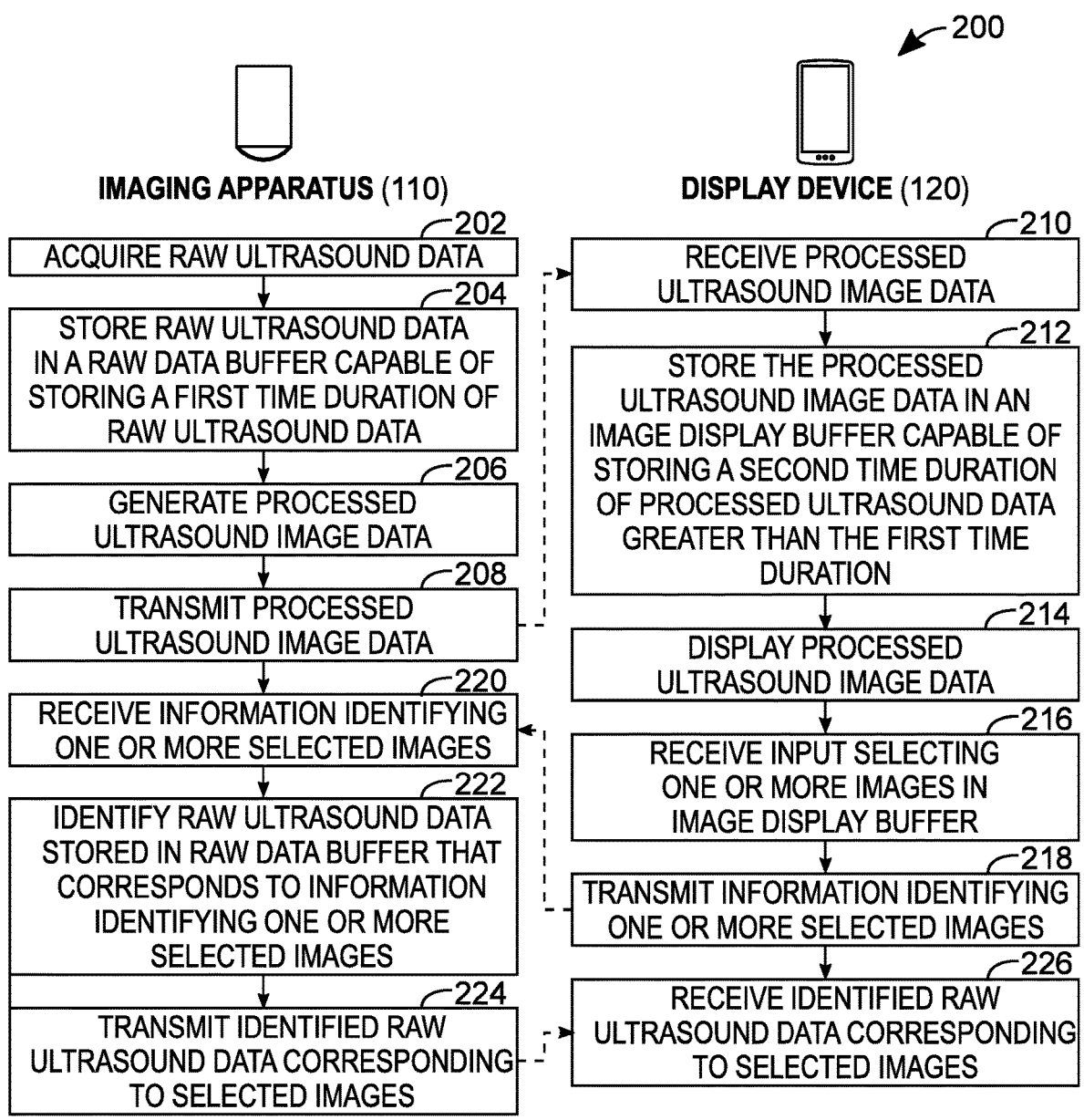
FIG. 2 is a flowchart diagram of a method for acquiring raw data from an ultrasound machine using a wirelessly connected device, in accordance with at least one embodiment of the present invention.

Referring to FIG. 2, shown there generally as 200, is a flowchart diagram of a method for acquiring raw data from an ultrasound machine using a wirelessly connected device, in accordance with at least one embodiment of the present invention. The method of FIG. 2 shows interactions between an imaging apparatus 110 and a display device 120 (e.g., as is shown in the FIG. 1). The various acts shown as being performed the respective processors 116, 126 on the imaging apparatus 110 and the display device 120. In discussing the various acts below, reference will also be made to the components of the system shown in FIG. 1. In various embodiments, the method may be implemented with a different system.

In various embodiments, the system 100 of FIG. 1 may be configured to provide a raw data acquisition mode that, when enabled, configures the imaging apparatus 110 to store raw data when acquiring and generating ultrasound images. When not enabled, the raw data may not be stored. For example, providing a raw data acquisition mode that only stores raw data when enabled may allow the imaging apparatus 110 to operate in a more efficient way when the retrieval of raw data is not required (e.g., by simply processing the raw data into processed image data in real time without saving a copy of the raw data into the raw data buffer for later retrieval). In various embodiments, the activation of the raw data acquisition mode may consist of allocating a raw data buffer and beginning to save ultrasound data into the raw data buffer. The "raw data acquisition mode" may also be referred to as the "raw ultrasound data collection mode" or simply, the "raw data collection mode" herein.

In some embodiments, prior to beginning the method of FIG. 2, a raw data acquisition mode of the system ultrasound system 100 may be enabled. As discussed below, the raw data acquisition mode may be activated in various ways. For example, this may be done in response to a request from the user. Additionally or alternatively, the raw data acquisition mode may be enabled automatically.

At 202, raw ultrasound data may be acquired by scanner 110. The raw ultrasound data may be digitized echo signals received from one or more transmission events. The raw ultrasound data may have some signal processing applied, such as adjustment of gain or filtering. The raw ultrasound data may include data from individual transducer elements 104. Alternatively or in addition, the raw ultrasound data may include post-beamformed data.

In various embodiments, acquisition settings may be controlled by processor 116. In some embodiments, acquisition settings are based on control signals received from display device 120.

At 204, raw ultrasound data may be stored in a raw data buffer 112. The raw ultrasound data may be stored with identifying information. The identifying information may include one or more of a frame number, timestamp, and/or other unique identifier.

At 206, ultrasound data may be processed. Various known or future developed processing steps may be applied. For example, processing steps may include one or more of the following: filtering, envelope detection, log compression, and scan conversion. As the ultrasound data is processed, identifying information may be included or tagged to identify which raw ultrasound data the processed data corresponds to.

In various embodiments, act 204 and act 206 may be performed simultaneously and/or iteratively.

As used herein, the raw ultrasound data may include individual channel radiofrequency data. However, in some embodiments, raw ultrasound data may also include other data after one or more preliminary operations have been performed on the individual channel radiofrequency data (but before the data has been transformed into processed ultrasound image data for transmission to the display device 110). For example, in various embodiments, raw ultrasound data may additionally or alternatively include beamformed radio frequency data and in-phase and quadrature (IQ) data.

The processed ultrasound image data nay be transmitted by imaging apparatus 110 at act 208 and received by display device 120 at act 210. For example, the processed ultrasound data may be transmitted between wireless interface 118 and wireless interface 128 using a suitable wireless communication protocol.

At 212, the processed ultrasound image data received at act 210 may be stored (e.g., in image display buffer 122 shown in FIG. 1). In some embodiments, the processed ultrasound image data may be provided in standard formats of digital images (e.g., Joint Photographic Experts Group (JPEG), Portable Network Graphics (PNG), or Tag Image File Format (TIFF)) and/or videos (e.g., Motion Picture Experts Group-4 (MP4) or Audio Video Interleave (AVI)).

In various embodiments, the raw data buffer 112 storing the raw data at the imaging apparatus 110 may be capable of storing a first time duration of raw ultrasound data, and the image display buffer 112 storing the processed image data at the display device 120 may be capable of storing a second time duration of processed ultrasound data greater than the first time duration. In other words, the number of images stored in image display buffer 112 at the display buffer 120 may exceed the number of image frames for which raw ultrasound data is stored in raw data buffer 112 on imaging apparatus 110. The relationship between the raw data buffer 112 and the image buffer 122 is illustrated and discussed in greater detail below with respect to FIG. 4.

At 214, the processed ultrasound image data may be displayed (e.g., on display 130 of display device 120). The ultrasound image data may be displayed such that it is substantially in real-time from acquisition (after accounting for processing and transmission delays). Alternatively, the ultrasound image data may be displayed while the imaging apparatus 110 is not actively acquiring, processing, and transmitting data. In various embodiments, the ultrasound image data may be displayed in a manner substantially similar to when a sequence of images is reviewed in a cine loop.

At 216, input may be received to select one or more images in image display buffer 122. For example, the input may be received while ultrasound data acquisition is active. Additionally or alternatively, the input may be received while ultrasound data acquisition is paused or stopped. An example user interface for receiving such input is discussed below with respect to FIG. 3. Additional example methods for selecting images are described below with reference to FIG. 6, in relation to the example user interface shown in FIG. 7.

At 218, information identifying one or more selected images is transmitted by display device 120. For example, the identifying information may include one or more frame numbers, timestamps, or unique identifiers. In various embodiments, the identifying information may be retrieved from metadata attached to the displayed processed ultrasound image data.

At 220, the information identifying one or more selected images may be received by imaging apparatus 110. In some embodiments, the reception of information identifying on or more selected images may be received while the ultrasound imaging device is still acquiring, processing, and transmitting ultrasound data display device 120. Additionally or alternatively, the reception of information identifying one or more selected images may be received while the ultrasound imaging device is in a 'Freeze' mode or otherwise not actively acquiring, processing, and transmitting ultrasound data.

At 222, raw ultrasound data may be identified at the imaging apparatus 110 that corresponds to information identifying one or more selected images. This may include matching the corresponding identifying information stored with the raw ultrasound data in act 204 to the identifying information received from the display device in act 220. In some embodiments, the identifying information may be cross-referenced from one type to another. For example, the identifying information received at act 220 may include one or more frame numbers and the corresponding raw ultrasound data may identified by a range of timestamps corresponding to the one or more frame numbers.

At 224, raw ultrasound data corresponding to the selected images may be transmitted by imaging apparatus 110. In various embodiments, the raw ultrasound data may be transmitted in an uncompressed format. However, in some embodiments, the raw ultrasound data may be compressed so as to allow the raw ultrasound data to be transmitted more quickly.

In various embodiments, the raw ultrasound data may be transmitted using the same wireless communication protocol by which the processed ultrasound image data is transmitted to display device 120 at act 208. However, in some embodiments, the raw ultrasound data may be transmitted using a different wireless communication protocol by which the processed ultrasound image data is transmitted.

At 226, raw ultrasound data corresponding to the selected images selected at act 216 may be received by display device 120. Upon reception, the raw ultrasound data may be stored in data storage 124 of the display device 120. In various embodiments, the received raw ultrasound data may be further uploaded to a server (e.g., a cloud service) so that it can be accessed by additional users.

Figure 3:
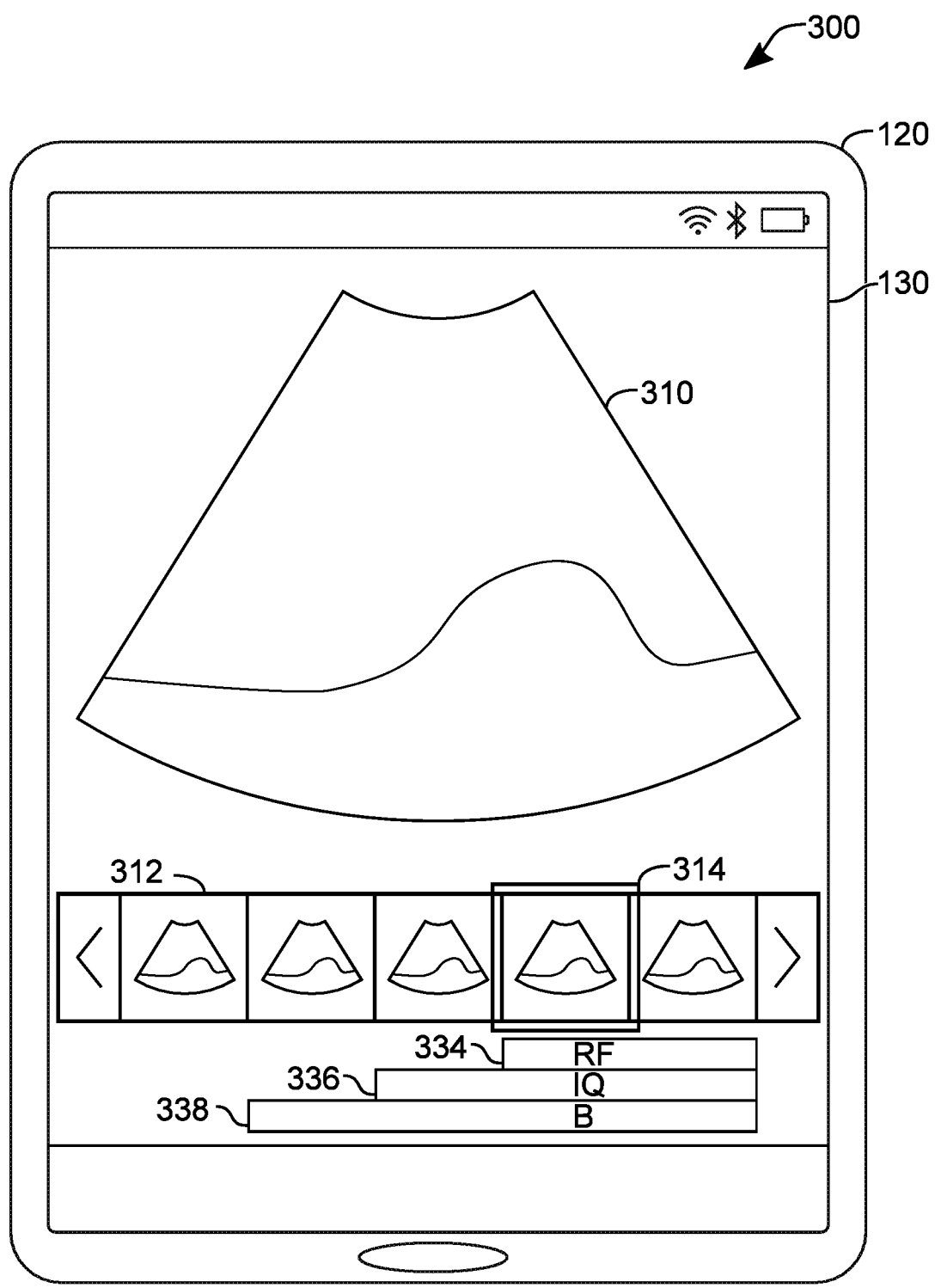
FIG. 3 is a view of a graphical user interface for selecting ultrasound image frames for which to retrieve corresponding raw ultrasound data, in accordance with at least one embodiment of the present invention.

Referring to FIG. 3, shown there generally as 300 is a view of an example graphical user interface for selecting ultrasound image frames for which to retrieve corresponding raw ultrasound data, in accordance with at least one embodiment of the present invention. The graphical user interface may be shown on display 130 of display device 120. As shown, the graphical interface may include an ultrasound image 310. The graphical interface may include an interface substantially similar to a screen for reviewing previously acquired and/or displayed ultrasound image data. This may be referred to as cine-review in various scenarios, for example.

The interface may include one or more controls for navigating a time-series of ultrasound image data, e.g., "scrubbing". The interface may include controls for stopping and pausing the playback of images, controlling the speed of playback, selecting a particular image frame, or incrementing or decrementing the frames. For example, the interface may include a slider control 312 that may show a miniature or thumbnail image of individual image frames of the processed ultrasound image data. In another embodiment, the slider control 312 may be provided as a simple line with a moving cursor, and as the moving cursor is moved, different image frames may be updated on the main ultrasound image 310 to show an image frame corresponding to the position of the cursor.

In addition to the conventionally known controls for navigating and controlling the display of ultrasound image cine loops, the user interface may include additional controls 314 for selecting one or more ultrasound images for which to acquire corresponding raw ultrasound data. For example, as illustrated the control 314 is provided as a box which may be expanded (e.g., via a pinch-out gesture) to select the frames for which to retrieve raw ultrasound data for. The user interface may include indicators 334, 336, 338 that convey whether raw ultrasound data is available for a particular ultrasound image frame in the cine-loop. In various embodiments, the raw data availability indicator may include a graphical element such as an icon.

In some embodiments, two or more types of raw ultrasound data may be available. The user interface may have additional indicators to indicate which types of raw ultrasound data are available for a particular ultrasound image frame. For example, the user interface may include RF data indicator 334, IQ data indicator 336 and B-mode data indicator 338. In some embodiments, the raw data indicators may be an on/off indicator (e.g., a flag or other graphical element) that indicates whether the data (or a certain type of raw ultrasound data) is available for a given frame. In some embodiments, the raw data indicators indicate for which portion of the entire ultrasound cine that raw data (of one or more raw ultrasound data types) is available. If the example user interface is used to navigate to previously-received ultrasound images for which there is no corresponding raw data available to be retrieved, it may display an image without the indicators 334, 336, 338 for those frames to indicate that no corresponding raw ultrasound data is available to be retrieved.

The interface may include a control for selecting one or more ultrasound images for which to acquire corresponding raw ultrasound data. The selection control may, for example, be a button that marks the currently displayed frame for raw data retrieval. The selection control may also be a control that enables the selection of a range of ultrasound image frames. The interface may also include a selection indicator for indicating which ultrasound image frames have been selected. The selection indicator may be separate from the selection control or may be combined. For example, the selection control may be a graphical indicator that changes shape (e.g., the rectangle 314 extending to encompass the selected frames) or color (e.g., so as to provide a highlighting effect) if the currently displayed image frame has been marked for raw ultrasound data retrieval.

The interface may include a control for initiating the raw ultrasound data retrieval process once one or more ultrasound images have been selected. This control may be provided in the form of a physical button on display device 120 or a control on the user interface.

In various embodiments, the number and type of ultrasound data stored in the raw data buffer may influence the duration for which the ultrasound images have corresponding raw data. For example, as noted above, raw ultrasound data may not necessarily just be channel domain or (pre-beamformed) radio frequency (RF) data. In various embodiments, raw ultrasound data may also include beamformed radio frequency data, in-phase and quadrature (IQ) data, and/or unprocessed B-mode data.

For a given image frame, the amount of storage capacity required to store the raw data may be reduced after successive preliminary operations are performed. For example, RF data may require the largest storage per image frame; IQ data may require less storage capacity, and unprocessed B-mode data even less. Given limited storage constraints at the imaging apparatus 110, since RF data may require the largest storage capacity per image frame, there may correspondingly be fewer image frames of processed image data for which such raw ultrasound data is available. However, for IQ data that requires less storage capacity than RF data, there may be more processed image frames for which IQ data is available. Further, since unprocessed B-mode data may require even less storage capacity than IQ data, there may be even more processed image frames for which unprocessed B-mode data is available.

This may result in an example user interface as is shown in FIG. 3: where the indicators for each of RF 334, IQ 336, and unprocessed B-mode 338 raw ultrasound data are positioned beneath the processed image frames for which such respective types of raw ultrasound data is available. The indicators 334, 336, 338 increase in number of frames from RF, to IQ, to unprocessed B-mode data to reflect the number of corresponding frames for which such corresponding raw ultrasound data is available. In the illustrated example, there is only 2 frames for which RF data is available, but there are 3 frames for which IQ data is available, and 4 frames for which unprocessed B-mode image data is available. It will be understood that other relationships amongst the different types of raw ultrasound data and their availability may be possible.

Figure 4:
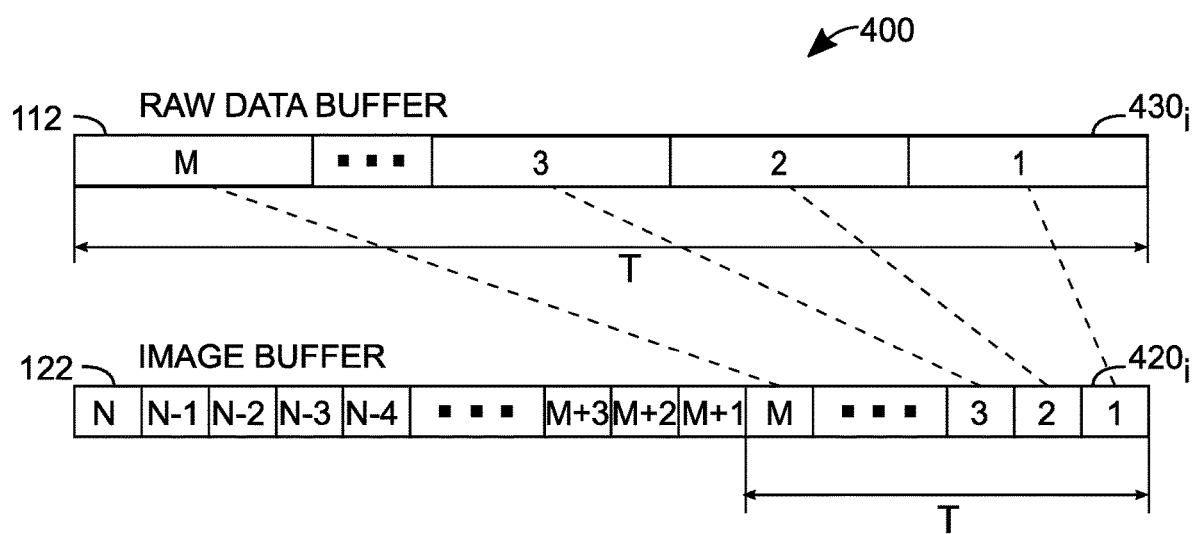
FIG. 4 is a schematic diagram of the image buffer and raw data buffer of FIG. 1, in accordance with at least one embodiment of the present invention.

Referring to FIG. 4, shown there generally as 400 is a schematic diagram of the image buffer and raw data buffer of FIG. 1, in accordance with at least one embodiment of the present invention. This embodiment illustrates a raw data buffer 112 (e.g., as provided on the imaging apparatus 110 shown in FIG. 1) capable of storing a first time duration of raw ultrasound data and an image buffer 122 (e.g., as provided on the display device 120 shown in FIG. 1) capable of storing a second time duration of processed ultrasound image data, where the second duration is greater than the first duration.

Raw data buffer 112 may be configured to store a number of raw ultrasound data frames $430_i$. The raw ultrasound data frames may be identified by a timestamp, a frame number, a universally unique identification number, and/or some other conventionally known or future developed means for determining for which ultrasound image frame the raw data corresponds to. In various embodiments, the size of the raw data buffer may be a fixed or adjustable during operation.

Image buffer 122 may be configured to store a number of ultrasound image frames $420_i$. The ultrasound image frames may similarly be identified by a timestamp, a frame number, a universally unique identification number, or some other conventionally known and/or future developed means for determining for which raw ultrasound data the image frame corresponds. In various embodiments, the size of image buffer 122 may be a fixed or adjustable during operation.

Raw ultrasound data may require larger storage capacity than the processed ultrasound image frames to which they correspond. Accordingly, for a given image buffer 122 capable of storing a number of processed ultrasound image frames, there may be 'N' frames that can be stored within the image buffer 122. However, since the storage of the corresponding raw ultrasound data requires more storage capacity, there may be only a subset 'M' of the 'N' processed image frames for which raw ultrasound data is available.

For example, as shown in FIG. 4, the image buffer 112 may have the capacity to store approximately 20 seconds worth of processed ultrasound image frames (e.g., image frames $420_1$-$420_N$). However, since the corresponding raw ultrasound data may require larger storage space, only a subset time duration of time 'T' (e.g., raw ultrasound frames $430_1$-$430_M$) can be stored in the raw data buffer 112. As shown in FIG. 4, processed ultrasound image frames '1', '2', '3' ... 'M' stored in the image buffer 122 and their corresponding raw ultrasound data (also labeled with corresponding labels '1', '2', '3', ... 'M') stored in the raw data buffer 112 are shown connected via dotted lines. Whereas the time 'T' only occupied a subset of the full time duration of frames of the image buffer 122, the same time duration of corresponding raw ultrasound data may occupy substantially all of the raw data buffer 112.

For example, in one example scenario, the raw data buffer 112 may be configured to store approximately time (T)=5 seconds of raw ultrasound data, which may correspond to a portion of the total time duration of processed ultrasound image frames (e.g., 20 seconds) that can be stored in the image buffer 122.

Notably, the present embodiments allow for a number of processed ultrasound image frames (e.g., $420_{M+1}$-$420_N$) to remain stored and accessible in the image buffer 122 even if there they have no corresponding raw ultrasound data to be retrieved from the raw data buffer 112. These image frames may constitute previously-received processed ultrasound image data that has no corresponding raw ultrasound data stored in the raw data buffer 112.

Unlike some traditional systems that transfer the raw ultrasound data to the display device 120 automatically upon a 'Freeze' operation, the present embodiments would not need to reserve space in the image buffer 122 to allow for the full breadth of the raw ultrasound data to be stored upon automatic transfer. Instead, that space in the image buffer 122 which would otherwise be reserved for storing raw ultrasound data upon automatic transfer can be used to store additional processed image frames so that a longer duration of cineloop can be navigated at the display device 120. By providing a user interface that indicates which subset of the processed ultrasound image frames in the image buffer 122 has corresponding raw data to be retrieved, the present embodiments may provide enhanced flexibility. For example, the present embodiments may allow processed ultrasound images to be generated, transferred, and reviewed in their normal course using the full time duration available with the smaller storage requirements of processed ultrasound image data. At the same time, raw ultrasound data for some of the processed ultrasound image frames may still nevertheless be retrieved upon selection in a suitable user interface (e.g., such as is shown in FIG. 3).

In further embodiments, the number of image frames stored in image buffer 122 may be restricted to a number smaller than its total capacity, or the image buffer size may be reduced, so that all images in the image buffer have corresponding raw ultrasound data in the raw data buffer. The change in the number of images that that image buffer 122 is configured to store may be changed dynamically, for example by enabling a raw data collection mode.

In the examples noted above, the image frames for which to obtain raw ultrasound data may be selected after they are displayed on display device 120. To facilitate the identification of the raw data corresponding to the processed ultrasound image frames, raw data availability information may be sent together with the images frames, for example in a meta tag. Additionally or alternatively, raw data availability may be requested from the imaging device 110 in additional communications (not shown) between the imaging apparatus 110 and the display device 120.

In the embodiments described above, a raw data acquisition mode can be enabled prior to performing the method of FIG. 2. Raw ultrasound data can then be stored in the raw data buffer 112 as processed ultrasound image data is being generated and transmitted. Using an example user interface such as is shown in FIG. 3, the display device 120 may then receive input to select which of the processed image frames to retrieve raw ultrasound data for. This may be considered a way of retrospectively retrieving raw ultrasound data after processed ultrasound data has already been transmitted from the imaging apparatus 110 to the display device 120.

However, in another aspect, the present embodiments may allow for different ways of enabling raw data acquisition mode and/or selecting processed ultrasound image frames for which to retrieve raw ultrasound data. These various aspects of the present embodiments are discussed generally below with respect to the methods shown in FIGS. 5-8.

Figure 5:
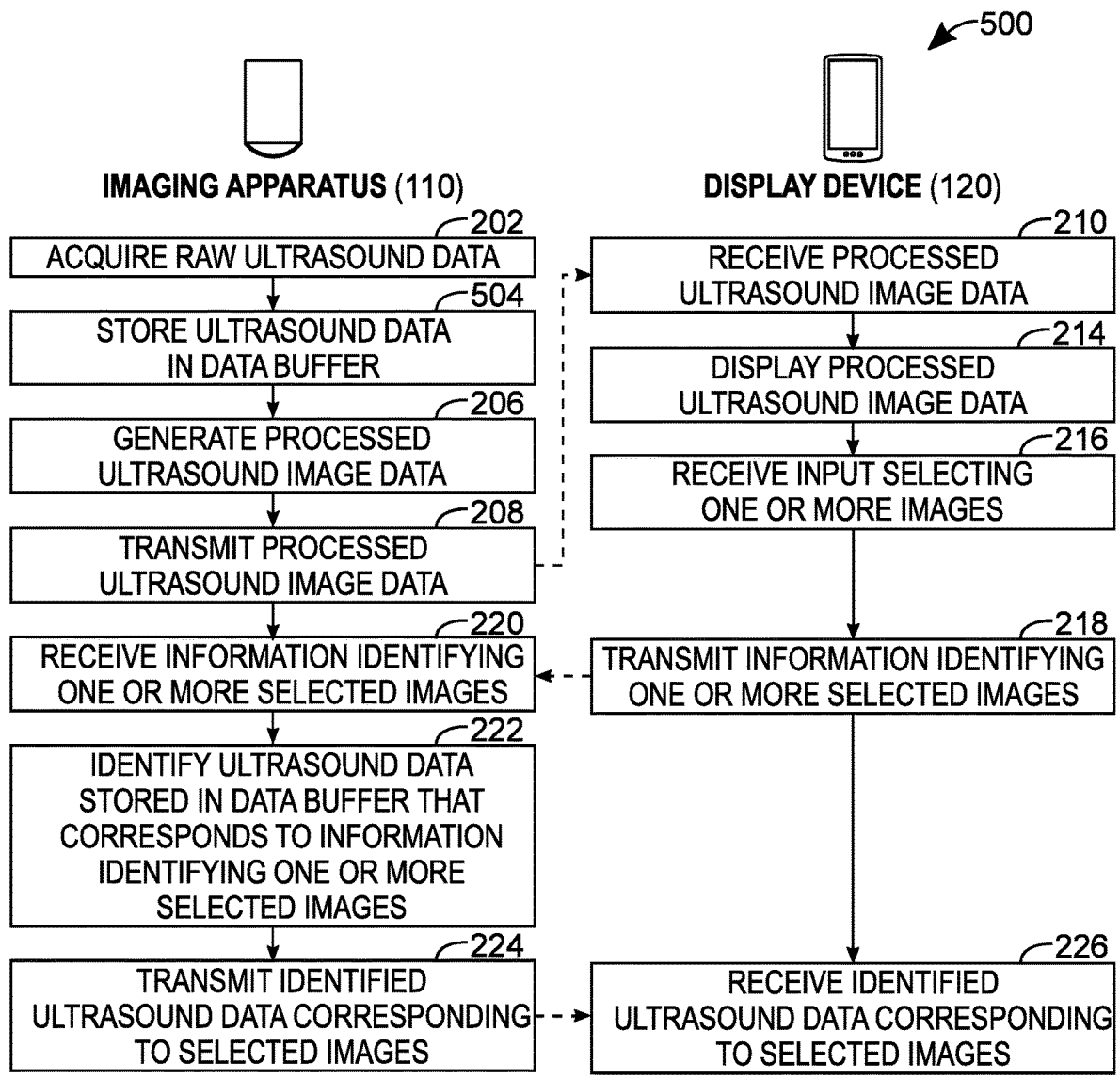
FIG. 5 is a flowchart diagram of a method for acquiring raw data from an ultrasound machine using a wirelessly connected device, in accordance with at least another embodiment of the present invention.

Referring to FIG. 5, shown there generally as 500 is a flowchart diagram of a method for acquiring raw data from an ultrasound machine using a wirelessly connected device, in accordance with at least another embodiment of the present invention. The method of FIG. 5 is a more generalized version of FIG. 2, where the acts of FIG. 5 with analogous reference numerals to that shown in FIG. 2 may be performed in a substantially similar manner.

The method of FIG. 5 differs from the method of FIG. 2 in at least two ways. First, at 504, raw ultrasound data is stored in a raw data buffer 112. However, the raw data buffer may not have any restrictions on the size of the raw data buffer 112, as there was in act 204 of FIG. 2. Second, act 212 can be omitted; specifically, there is no requirement to store the processed ultrasound image data in an image buffer, and there is no restriction on the size of the image buffer. As discussed below, different ways of enabling raw data acquisition mode and/or selecting processed ultrasound image frames for which to retrieve raw ultrasound data may be performed with this more generalized method shown in FIG. 5 (e.g., by modifying one or more of the acts).

Figure 6:
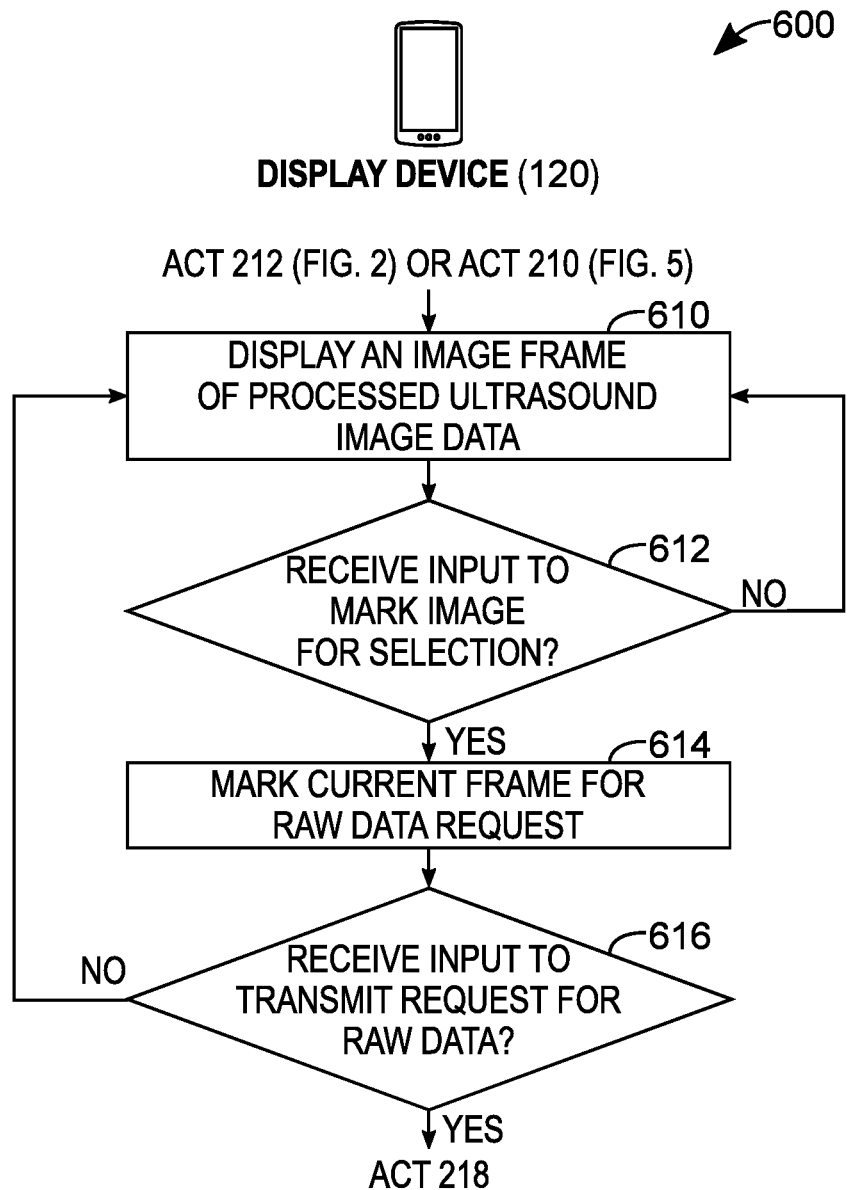
FIG. 6 shows a flowchart diagram of certain acts for selecting and retrieving raw ultrasound data, in accordance with at least one embodiment of the present invention.

Referring to FIG. 6, shown there generally as 600 is a flowchart diagram of certain acts for selecting and retrieving raw ultrasound data, in accordance with at least one embodiment of the present invention. Whereas the methods of FIGS. 2 and 5 have acts 214-216 that first display processed ultrasound image data (act 214) and then receive input for selecting the one or more images in the image display buffer for which to retrieve raw ultrasound data (act 216), it may be possible to replace acts 214-216 in these methods with the acts shown in FIG. 6 so that another way of identifying image frames for retrieving raw ultrasound data can be performed. As illustrated, the acts shown in FIG. 6 may be performed by the display device 120 after act 212 of FIG. 2 or after act 210 of FIG. 5.

At 610, an image frame of processed ultrasound image data can be displayed on display 130 of display device 120. Act 610 may be performed in a manner substantially similar to the manner in which act 214 in FIGS. 2 and 5 is performed for displaying images; however, instead of displaying stream of received processed ultrasound images, a single image frame is displayed and the method can proceed to act 612.

At 612, the method may be configured to monitor for input that marks the displayed image for selection. For example, the input may be received via input module 132 on display device 120 (e.g., as is shown in FIG. 1). In an example embodiment, the input may be received via a button on a user interface that can be pressed as processed ultrasound image frames are continually being displayed. If such a button is pressed (or held down) while a processed ultrasound image is being displayed, that can be considered the input for marking an image for selection at act 612. If no input is received, the ultrasound system returns to act 610 to display the next image.

If the input to mark an image for selection is received at act 612, the method may proceed to act 614 to mark the currently displayed frame for a raw data retrieval. The current frame may be marked by reading and storing identifying information of the ultrasound image (e.g., frame number, timestamp, and/or other suitable identifying information—as discussed above). Additionally or alternatively, the marked frame may also be stored in a separate image buffer. In some embodiments, marking the currently displayed image may additionally or alternatively involve sending a save request to the imaging apparatus 110. The save request may prevent the raw ultrasound data corresponding to the current frame in the raw data buffer from being overwritten. After marking a current image for selection to retrieve corresponding raw ultrasound data, the method may proceed to act 616.

At 616, the method may involve monitoring for input to transmit a request for retrieving raw ultrasound data of any images(s) marked for selection. If no input is received, the method may return to act 214 to continue displaying subsequent image frames of the processed ultrasound image data and monitoring for input that marks displayed processed image frames for retrieving corresponding raw ultrasound data. If input is received, the method may proceed to act 218 of the methods of FIG. 2 or 5, and information identifying the one or more selected images can be transmitted to the imaging apparatus 110.

The input received at act 216 may differ in various embodiments. For example, input may be provided in the form of a 'Retrieve' button on a user interface that is enabled once at least one frame is marked for selection. If pressed, this may allow the method to proceed to act 218, as noted. In another embodiment, the pressing of a 'Freeze' button on a user interface may constitute the input for act 216. Since the pressing of a 'Freeze' button may stop transmittal of processed ultrasound image data to the display device 120, bandwidth in the communication link between the imaging apparatus 110 and the display device 120 may be freed up so as to allow the raw ultrasound data for the selected image frames to be provided to the display device 120. Unlike the embodiment discussed above with respect to FIG. 3 where a user interface allows for selection of processed ultrasound image frames for retrieving raw ultrasound data retrospectively after the processed ultrasound image frames are displayed, the acts of FIG. 6 allow for marking of processed ultrasound images for selection as they are being displayed. The acts of FIG. 6 may thus be considered a method of prospectively selecting the processed ultrasound images for which to retrieve raw ultrasound data.

In certain instances, the acts of FIG. 6 may be considered a method of selecting the image frames for which to obtain raw ultrasound data in substantially real-time to when they are displayed. As noted, during the real-time display of images, the display device 120 may receive an input from the user to request raw ultrasound data for the current frame. Pressing the raw data button on the use interface 'marks' the current image frame. (e.g. saves the timestamp). Once imaging is stopped (e.g. through 'Freeze' button push), the list of timestamps is sent to the probe to retrieve the raw data.

Figure 7:
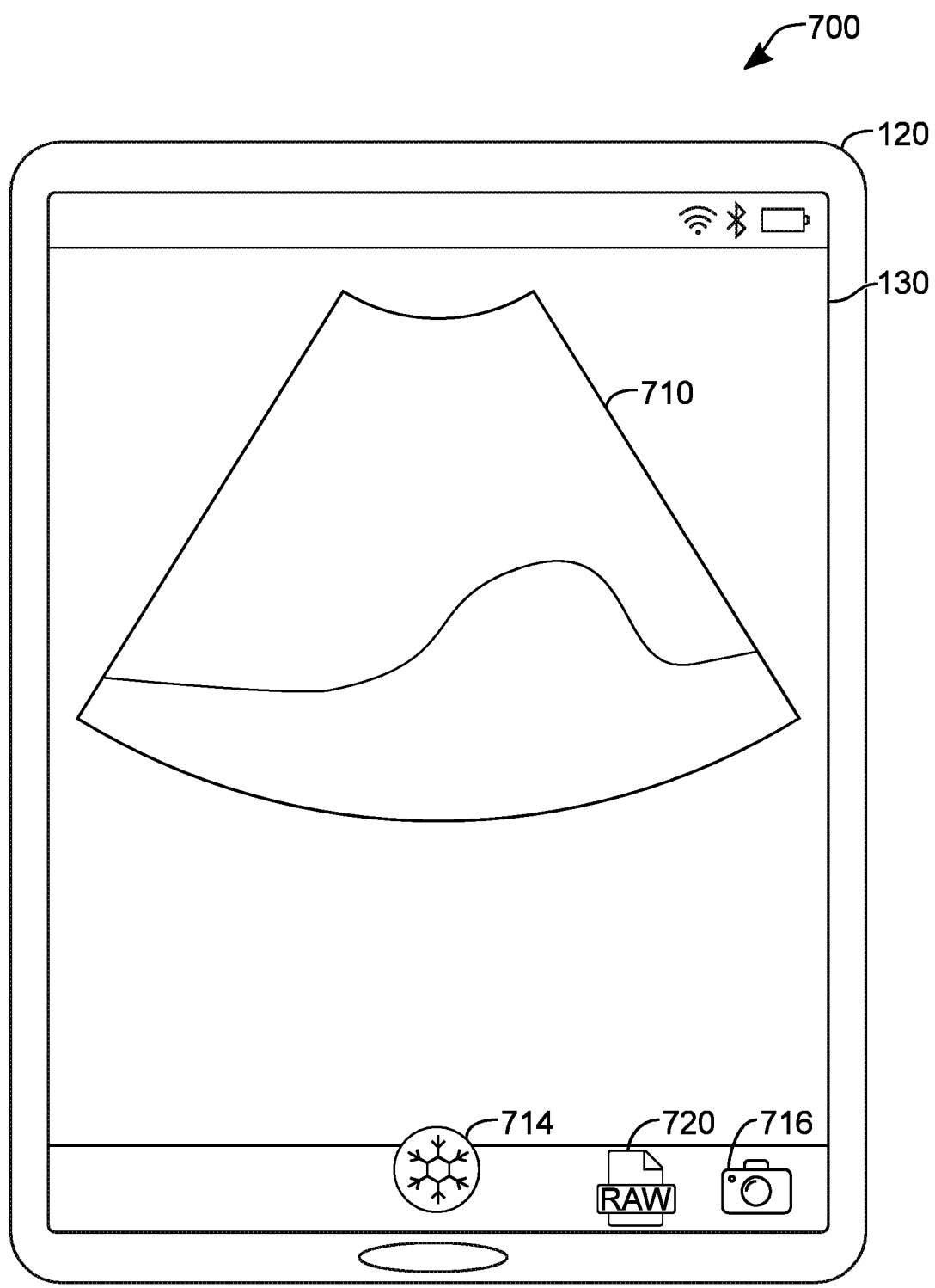
FIG. 7 shows a view of a graphical user interface for retrieving raw ultrasound data, in accordance with at least one embodiment of the present invention.

Referring to FIG. 7, shown there generally as 700 is a view of a graphical user interface for retrieving raw ultrasound data, in accordance with at least one embodiment of the present invention. The graphical user interface may be shown on display 130 of user interface device 120 and may include an ultrasound image 710. The ultrasound image 710 may be a live stream of images transmitted from the imaging apparatus 110 and shown substantially in real-time.

The graphical interface may include controls for controlling the ultrasound imaging apparatus 110 (e.g., ultrasound image data acquisition parameters) and interacting with the acquired and displayed ultrasound image(s). For example, a 'Freeze' button 714 (shown as a snowflake icon in FIG. 7) may be used to start and stop image acquisition, and a capture button 716 may be provided to save the currently displayed image.

The graphical interface may include one or more additional controls for enabling, selecting, and requesting raw ultrasound data. For example, a raw data request button 720 may be provided to mark a currently displayed frame for raw ultrasound data retrieval. An input via this button 720 may, for example, constitute the input to be received at act 612 of FIG. 6. In various embodiments, the pressing of this button 720 may additionally or alternatively initiate the start of a raw data acquisition mode. For example, as discussed below, this button 720 may constitute the signal being monitored for at act 822 of FIG. 8.

Figure 8:
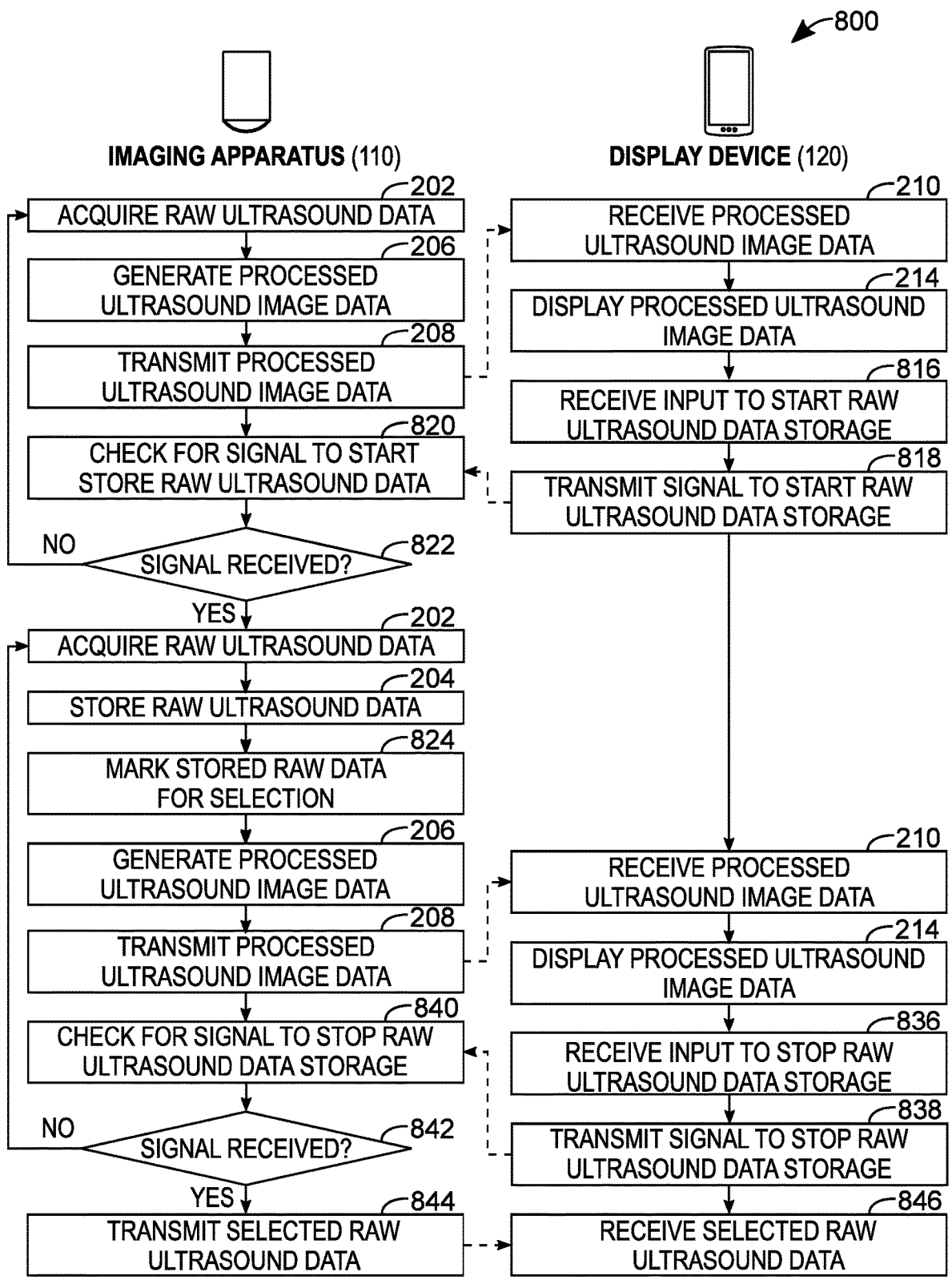
FIG. 8 is a flowchart diagram of a method for acquiring raw data from an ultrasound machine using a wirelessly connected device, in accordance with at least another embodiment of the present invention.

As discussed above, prior to initiating the methods of FIG. 2 and FIG. 5 the imaging apparatus 110 may have received input to begin operating in a raw data acquisition mode. In various embodiments, the ultrasound system 100 may be operable both in a mode where raw ultrasound data is not stored (e.g., a normal imaging mode) and a mode where raw ultrasound data is stored (e.g., a raw data acquisition mode). Limiting the storage of raw ultrasound data to only the periods when it is required may help conserve battery power. This may allow the imaging apparatus 110 to operate more efficiently since it does not need to allocate the raw data buffer 112 for storing raw ultrasound data of processed ultrasound images. In various embodiments, the raw data acquisition mode can be explicitly enabled (e.g., in a settings menu of a software application configured to communicate with the imaging apparatus 110). FIG. 8 illustrates a method where a raw ultrasound data acquisition mode can be prospectively enabled as processed ultrasound images are being displayed at the display device 120.

Referring to FIG. 8, shown there generally as 800 is a flowchart diagram of a method for acquiring raw data from an ultrasound machine using a wirelessly connected device, in accordance with at least another embodiment of the present invention. In this embodiment, ultrasound system 100 is operable in both a normal imaging mode and a raw data acquisition mode. The method of FIG. 8 may also provide prospective automated selection of the image frames for which to acquire and transmit corresponding raw ultrasound data.

In the method of FIG. 8, ultrasound system 100 may start in a normal imaging mode. Acts 202, 206, 208, 210 and 214 in FIG. 8 may be performed in a manner similar to the way acts 202, 206, 208, 210 and 214, respectively, were described as being performed with reference to FIG. 2. However, in this embodiment, raw ultrasound data is not stored at this stage of operation.

At 816, input may be received to start raw ultrasound data storage at the display device 120 (e.g., to enable raw data acquisition mode), and a signal may be transmitted to start raw ultrasound data storage at act 818. The transmission of the signal at act 818 may be considered an example of the display device 120 directing the imaging apparatus 110 to activate the raw ultrasound data collection mode at the imaging apparatus 110. The input may be received through input module 132 at display device 120 (as shown in FIG. 1). For example, as noted above, the user interface control 720 described with reference to FIG. 7 may be used.

At 820, imaging apparatus 110 may check if a signal to start raw ultrasound data storage was received. At 822, if a signal to start raw ultrasound data storage was received at act 820, imaging apparatus 110 may switch to operate in a raw data acquisition mode (the 'YES' branch at 822). If a signal to start raw ultrasound storage was not received, imaging apparatus 110 may continue to operate in the normal imaging mode and return to acquire raw ultrasound data at act 202 (the 'NO' branch at 822).

While operating in raw data acquisition mode, imaging apparatus 110 may perform act 202 and 204 in a manner similar to act 202 and 204 described with reference to FIG. 2.

At 824, the stored raw ultrasound data may be marked for selection. In this embodiment, no secondary selection process on the display device may be necessary. Various criteria may be used to select which raw ultrasound data are marked for selection. In some embodiments, substantially all raw ultrasound data acquired while operating in raw data acquisition mode may be marked for selection. In other embodiments, predetermined criteria may be used to select a subset of the acquired raw ultrasound data. For example, the predetermined criteria may indicate that every $n^{th}$ frame is to be stored (where 'n' is a positive integer) so as to allow raw ultrasound data to be stored over a longer time duration (given a limited size of raw data buffer 112).

After act 824, method 800 of FIG. 8 may continue to perform acts 206, 208, 210 and 214 in a manner similar to acts 206, 208, 210 and 214 as described with reference to FIG. 2 to acquire, process, transmit, and display processed ultrasound image data on display device 120. Imaging apparatus 110 may continue to acquire, store, and transmit processed ultrasound image data until a signal to stop raw ultrasound data storage is received.

At 836, input may be received to stop raw ultrasound data storage. The input may be received via input module 132 on display device 130, for example. Alternatively, an input may be received based on the state of the display device 120. For example, raw ultrasound data storage may be stopped after a predetermined time has been reached, a certain number of frames have been acquired, and/or a certain volume of raw ultrasound data has been acquired. These thresholds on time, number of frames, and/or data volume may be configured or selected by the user, in various embodiments.

In some embodiments, the input to stop raw ultrasound data storage may also stop the acquisition, processing, transmission, and display of processed ultrasound image data. For example, a 'Freeze' control may be used to freeze imaging and also stop raw ultrasound data storage.

At 838, the signal to stop raw ultrasound data storage can be transmitted from display device 120 to imaging apparatus 110. The transmission of the signal at act 838 may be considered the display device directing the imaging apparatus 110 to deactivate the raw ultrasound data collection mode.

At 840, imaging apparatus 110 may check to see if a stop raw ultrasound data storage signal was received from display device 120. At 842, if a stop raw ultrasound data storage signal was not received at act 840, the imaging apparatus 110 may continue to acquire ultrasound data at act 202 (the 'NO' branch at 842). If a stop raw ultrasound data storage signal was received, imaging apparatus 110 continues to act 844 (the 'YES' branch at 842).

At 844, the marked raw ultrasound data can be transmitted to display device 120 (e.g., using the connection 140 shown in FIG. 1). At 846, the raw ultrasound data may be received from the imaging apparatus 110. Upon receipt, the selected raw ultrasound data may be stored in data storage 124. The method of FIG. 8 may provide a simplified example embodiment where the raw data acquisition mode and the marking of processed ultrasound images can be prospectively performed with a single user interface control. For example, this may reduce the number of navigational steps needed to obtain raw ultrasound data for desired processed image frames, and thereby enhance ease and simplicity of operation. In some instances, the method of FIG. 8 may also be considered to be selecting processed ultrasound image(s) for raw data acquisition in substantially real-time while processed ultrasound images are being transmitted from the imaging apparatus 110 and displayed at the display device 120.

The generation and transmission of processed ultrasound images in the normal imaging mode may be considered the generation and transmission of an ultrasound image feed of processed ultrasound images for display at the display device 120. In various embodiments, when input to activate a raw data collection mode is received at act 816 and transmitted to the imaging apparatus 110 at act 818, the imaging apparatus 110 may continue to generate and transmit the ultrasound image feed, and the processed ultrasound images being transmitted and received at acts 208 and 210 during the raw data collection mode may be considered part of the same ultrasound image feed.

In various embodiments, the signal to start the raw data acquisition mode transmitted at act 818 can be configured to be lightweight and small in size. This may allow the signal to be transmitted to the imaging apparatus 110 without consuming much bandwidth in the communication link 140. The lightweight nature of the signal may also allow the signal to be received by the imaging apparatus 110 without the imaging apparatus 110 incurring much processing overhead. As a result, the imaging apparatus 110 may be able to transition into the raw data collection mode without causing substantial delay in the generation and transmission of the ultrasound image feed. The viewing of the ultrasound image feed at the display device 120 may likewise proceed without substantial delay in displaying successive frames of the ultrasound image feed.

The method of FIG. 8 may be considered an instance where the imaging device 110 can be instructed to acquire raw ultrasound data for a number of frames before the imaging frames have been acquired. For example, the imaging device 110 may be instructed to acquire one or more ultrasound image frames and to store one or more sets of ultrasound data corresponding to the image frames as the raw ultrasound data is being acquired and processed into processed ultrasound image frames.

In the embodiments described above where selection of processed images may be performed prospectively (e.g., FIG. 6 or FIG. 8), it may be possible to configure the storage of raw ultrasound data to be performed according to a predetermined criterion while a user interface control is being activated. For example, the selection of one or more frames may be requested based on the following: a certain number of frames (e.g., 10 frames), a certain time frame (e.g., 10 seconds), and/or a proportion of available storage capacity (e.g., 75% of the raw data buffer 112, or 50% of data storage 124). In another example of a predetermined criteria, the frames for which raw ultrasound data is stored need not be contiguous. For example, raw ultrasound data may be stored for every $j^{th}$ image frame (e.g., where j is a positive integer greater than 1), or every k seconds (e.g., where k is a positive number greater than 0).

Figure 9:
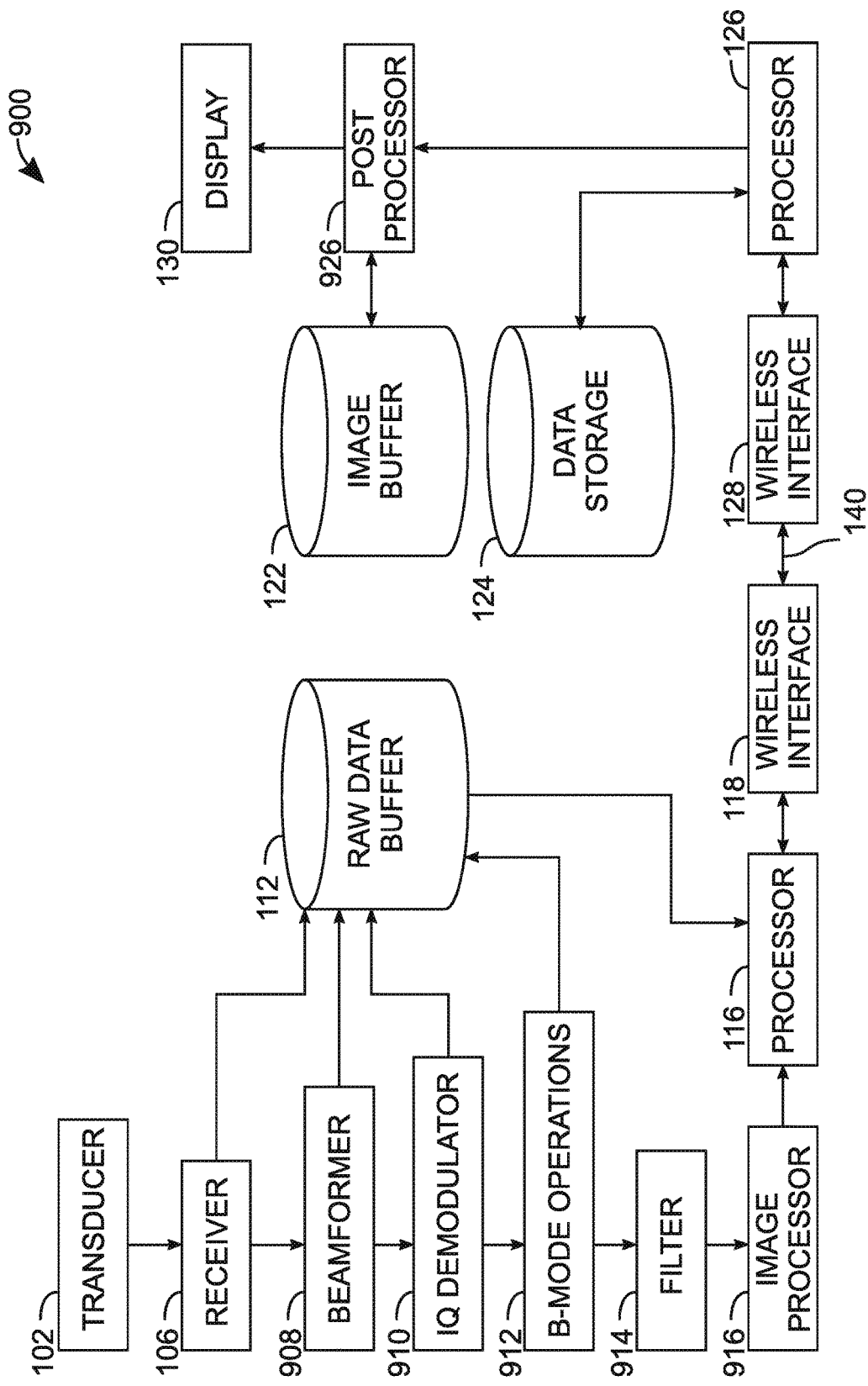
FIG. 9 is a data flow diagram of a method for selecting and retrieving raw ultrasound data from an ultrasound machine using a wirelessly connected device, in accordance with at least one embodiment of the present invention.

Referring to FIG. 9, shown there generally as 900 is a data flow diagram of FIG. 9 is a data flow diagram of a method for selecting and retrieving raw ultrasound data from an ultrasound machine using a wirelessly connected device, in accordance with at least one embodiment of the present invention. FIG. 9 shows how raw ultrasound data of various types and forms (e.g., as discussed above, after various preliminary operations have been performed) may be stored in raw data buffer 112. Some elements that were previously shown in FIG. 1 are also referred to in FIG. 9.

Reflected ultrasound energy may be converted into electrical energy by transducer 102 and digitized by receiver 106. The digitized data may then have several preliminary operations applied. The digitized data may be beamformed in beamformer 908, and then demodulated into in-phase and quadrature data in IQ demodulator 910. Additional preliminary operations such as forming into a B-mode image by B-Mode operations 912, filtering in filter 914 and/or additional image processing in image processor 916 may be performed.

Processor 116 may store ultrasound data to raw data buffer 112 after any one or more of the preliminary operations. For example, pre-beamformed channel data from receiver 106 may be stored in raw data buffer 112. In another example, beamformed data from beamformer 908 and/or corresponding IQ data from IQ demodulator 910 may be stored in raw data buffer 112. Further, data after B-mode operations have been performed may also be stored in raw data buffer 112. When more than one type of raw ultrasound data is stored, the data may be stored together or they may be stored separately.

Processed ultrasound image data may be transmitted from wireless interface 118 to wireless interface 128 via communication link 140. Once received at the wireless interface 128, the processed ultrasound image data may be provided to processor 126, and subsequently to post processor 926 so that additional processing steps (e.g., scan conversion) can be applied. The processed ultrasound image data may be buffered in image buffer 122 and displayed on display 130.

Pursuant to the discussion above, processor 126 may make a request to processor 116 for raw ultrasound data. Processor 116 may retrieve the requested raw ultrasound data from raw data buffer 112 and transmit the selected raw ultrasound data through wireless interface 118 to wireless interface 128. The retrieved raw ultrasound data may then be stored in data storage 124.

In various embodiments, greater or fewer of the preliminary operations may be completed on the display device 120. For example, in some embodiments, B-mode operations 912, filter 914, and image processor 916 may be implemented on the display device 120 such that beamformed RF data and/or IQ data is transmitted when a request for raw ultrasound data is made.

As will be appreciated upon reading this description, the apparatus, systems and methods described herein may help to alleviate some drawbacks of traditional ultrasound systems. The embodiments described herein may enable an ultrasound operator to retrieve raw ultrasound data corresponding from a wireless ultrasound probe which corresponds to displayed ultrasound image data. For example, an ultrasound operator may select one or more ultrasound images within a cine loop and retrieve the corresponding raw ultrasound data from a wirelessly connected probe. The present embodiments may enable a higher frame rate and image quality for real-time image display than if raw ultrasound data was attempted to be transmitted simultaneously. Further, the embodiments described herein may provide the advantage of access to raw ultrasound data for more advanced processing or research while still benefiting from the advantages of a wireless probe such as improved ergonomics.

While a number of exemplary aspects and embodiments have been discussed above, those of skill in the art will recognize that may be certain modifications, permutations, additions and sub-combinations thereof. While the above description contains many details of example embodiments, these should not be construed as essential limitations on the scope of any embodiment. Many other ramifications and variations are possible within the teachings of the various embodiments.

INTERPRETATION OF TERMS

Unless the context clearly requires otherwise, throughout the description and the
"comprise", "comprising", and the like are to be construed in an inclusive sense, as opposed to an exclusive or exhaustive sense; that is to say, in the sense of "including, but not limited to";
"connected", "coupled", or any variant thereof, means any connection or coupling, either direct or indirect, between two or more elements; the coupling or connection between the elements can be physical, logical, or a combination thereof;
"herein", "above", "below", and words of similar import, when used to describe this specification, shall refer to this specification as a whole, and not to any particular portions of this specification;
"or", in reference to a list of two or more items, covers all of the following interpretations of the word: any of the items in the list, all of the items in the list, and any combination of the items in the list;
the singular forms "a", "an", and "the" also include the meaning of any appropriate plural forms.

Unless the context clearly requires otherwise, throughout the description and the claims:
Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

Embodiments of the invention may be implemented using specifically designed hardware, configurable hardware, programmable data processors configured by the provision of software (which may optionally comprise "firmware") capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs"), and the like. Examples of configurable hardware are: one or more programmable logic devices such as programmable array logic ("PALs"), programmable logic arrays ("PLAs"), and field programmable gate arrays ("FPGAs"). Examples of programmable data processors are: microprocessors, digital signal processors ("DSPs"), embedded processors, graphics processors, math co-processors, general purpose computers, server computers, cloud computers, mainframe computers, computer workstations, and the like. For example, one or more data processors in a control circuit for a device may implement methods as described herein by executing software instructions in a program memory accessible to the processors.

For example, while processes or blocks are presented in a given order herein, alternative examples may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed at different times.

The invention may also be provided in the form of a program product. The program product may comprise any non-transitory medium which carries a set of computer-readable instructions which, when executed by a data processor (e.g., in a controller and/or ultrasound processor in an ultrasound machine), cause the data processor to execute a method of the invention. Program products according to the invention may be in any of a wide variety of forms. The program product may comprise, for example, non-transitory media such as magnetic data storage media including floppy diskettes, hard disk drives, optical data storage media including CD ROMs, DVDs, electronic data storage media including ROMs, flash RAM, EPROMs, hardwired or pre-programmed chips (e.g., EEPROM semiconductor chips), nanotechnology memory, or the like. The computer-readable signals on the program product may optionally be compressed or encrypted.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples, but should be given the broadest interpretation consistent with the description as a whole.

What is claimed is:

1. A method for acquiring raw ultrasound data from an ultrasound machine using a wirelessly connected device, the method comprising, at the wirelessly connected device:
    receiving processed ultrasound image data from the ultrasound machine, wherein the received processed ultrasound image data corresponds to and is processed from raw ultrasound data stored in a raw data buffer at the ultrasound machine, wherein the raw data buffer stores a first time duration of raw ultrasound data, and the received processed ultrasound image data requires less storage capacity than the corresponding raw ultrasound data stored in the raw data buffer;
    storing the processed ultrasound image data in an image display buffer, the image display buffer stores a second time duration of processed ultrasound image data longer than the first time duration, and wherein the image display buffer simultaneously stores: (i) the received processed ultrasound image data corresponding to the raw ultrasound data stored in the raw data buffer, and (ii) previously-received processed ultrasound image data that has no corresponding raw ultrasound data stored in the raw data buffer;
    receiving input selecting one or more images of the received processed ultrasound image data stored in the image display buffer, wherein (i) the received processed ultrasound image data, stored in the image display buffer, corresponding to the raw ultrasound data stored in the raw data buffer at the ultrasound machine and (ii) the previously-received processed ultrasound image data, stored in the image display buffer, that has no corresponding raw ultrasound data stored in the raw data buffer, are both viewable in a user interface of the wirelessly connected device, the user interface for navigating images stored in the image display buffer, and wherein prior to receiving input selecting the one or more images, the user interface displays an image of the processed ultrasound image data stored for the second time duration, and wherein the user interface indicates for the displayed image whether there exists to be retrieved, in the first time duration, corresponding raw ultrasound data stored in the raw data buffer in the ultrasound machine;
    transmitting information identifying the selected one or more images to the ultrasound machine, wherein the ultrasound machine identifies the raw ultrasound data, stored in the raw data buffer, that corresponds to the selected one or more images, for return to the wirelessly connected device; and
    receiving the identified raw ultrasound data corresponding to the selected one or more images.

2. The method of claim 1, wherein prior to receiving input selecting the one or more images, the user interface is configured to display an image from the previously-received processed ultrasound image data, and wherein the user interface does not indicate that corresponding raw ultrasound data is available to be retrieved from the ultrasound machine.

3. The method of claim 1, further comprising:
    storing the received raw ultrasound data, corresponding to the selected one or more images, in a storage location different from the image display buffer.

4. The method of claim 1, wherein prior to receiving the processed ultrasound image data, the method further comprises:
    receiving input indicating a raw ultrasound data collection mode of the ultrasound machine is to be activated; and
    directing the ultrasound machine to activate the raw ultrasound data collection mode.

5. The method of claim 4, wherein prior to receiving the input indicating the raw ultrasound data collection mode is to be activated, the method further comprises:
    operating in an imaging mode where the previously-received processed ultrasound image data is received, and no corresponding raw ultrasound data is stored in the raw data buffer at the ultrasound machine.

6. The method of claim 4, wherein prior to receiving the input indicating the raw ultrasound data collection mode of the ultrasound machine is to be activated, the method further comprises:
    receiving an ultrasound image feed comprising the previously-received processed ultrasound image data; and
    displaying the ultrasound image feed;
    and wherein during receipt of the input indicating the raw ultrasound data collection mode at the ultrasound machine is to be activated, the method further comprises:
    continuing to receive and display the ultrasound image feed, the ultrasound image feed comprising the received processed ultrasound image data.

7. The method of claim 6, wherein the ultrasound image feed is continued to be received and displayed when the raw ultrasound data collection mode is activated without substantial delay in displaying successive frames of the ultrasound image feed.

8. The method of claim 4, wherein after the received processed ultrasound image data is stored in the image display buffer, the method further comprises:
    receiving input indicating the raw ultrasound data collection mode of the ultrasound machine is to be deactivated; and
    directing the ultrasound machine to deactivate the raw ultrasound data collection mode.

9. The method of claim 8, wherein the input indicating the raw ultrasound data collection mode of the ultrasound machine is to be activated comprises pressing of a button on a user interface provided on one of the ultrasound machine and the wirelessly connected device, and the received input indicating the raw ultrasound data collection mode of the ultrasound machine is to be deactivated comprises a release of the button.

10. The method of claim 1, wherein prior to receiving the input selecting one or more images from the received processed ultrasound image data stored in the image display buffer, the method further comprises:
receiving input to stop ultrasound data acquisition at the ultrasound machine; and
directing the ultrasound machine to stop ultrasound data acquisition.

11. A method for transmitting raw ultrasound data from an ultrasound machine to a wirelessly connected device, the method comprising, at the ultrasound machine:
acquiring raw ultrasound data;
storing the acquired raw ultrasound data in a raw data buffer, wherein the raw data buffer stores a first time duration of raw ultrasound data;
generating processed ultrasound image data from the raw ultrasound data, the processed ultrasound image data requiring less storage capacity than the acquired raw ultrasound data;
transmitting the processed ultrasound image data to the wirelessly connected device, wherein the transmitted processed ultrasound image data is stored at the wirelessly connected device in an image display buffer, the image display buffer stores a second time duration of processed ultrasound image data longer than the first time duration, and wherein the image display buffer simultaneously stores: (i) the transmitted processed ultrasound image data corresponding to and processed from the raw ultrasound data stored in the raw data buffer, and (ii) previously-transmitted processed ultrasound image data that has no corresponding raw ultrasound data stored in the raw data buffer;
receiving, from the wirelessly connected device, information identifying one or more images selected from the transmitted processed ultrasound image data, wherein (i) the received processed ultrasound image data, stored in the image display buffer, corresponding to the raw ultrasound data stored in the raw data buffer at the ultrasound machine and (ii) the previously-received processed ultrasound image data, stored in the image display buffer, that has no corresponding raw ultrasound data stored in the raw data buffer, are both viewable in a user interface of the wirelessly connected device, the user interface for navigating images stored in the image display buffer, and wherein prior to receiving input selecting the one or more images, the user interface displays an image of the processed ultrasound image data stored for the second time duration, and wherein the user interface indicates for the displayed image whether there exists to be retrieved, in the first time duration, corresponding raw ultrasound data stored in the raw data buffer in the ultrasound machine;
identifying the raw ultrasound data, stored in the raw data buffer, corresponding to the one or more images; and
transmitting, to the wirelessly connected device, the raw ultrasound data, stored in the raw data buffer, corresponding to the one or more images.

12. The method of claim 11, wherein prior to storing the acquired raw ultrasound data in the raw data buffer, the method further comprises:
receiving direction from the wirelessly connected device that a raw ultrasound data collection mode of the ultrasound machine is to be activated; and
activating the raw ultrasound data collection mode.

13. The method of claim 12, wherein prior to receiving the direction from the wirelessly connected device that the raw ultrasound data collection mode is to be activated, the method further comprises:
operating in an imaging mode where the previously-transmitted processed ultrasound image data is generated, and no corresponding raw ultrasound data is stored in the raw data buffer.

14. The method of claim 12, wherein prior to receiving the direction from the wirelessly connected device that the raw ultrasound data collection mode is to be activated, the method further comprises:
generating an ultrasound image feed comprising the previously-transmitted processed ultrasound image data; and
transmitting the ultrasound image feed to the wirelessly connected device;
and wherein upon receipt of the direction from the wirelessly connected device that the raw ultrasound data collection mode is to be activated, the method further comprises:
continuing to generate and transmit the ultrasound image feed, the ultrasound image feed comprising the transmitted processed ultrasound image data.

15. The method of claim 14, wherein the ultrasound image feed is continued to be generated and transmitted without substantial delay in transmitting successive frames of the ultrasound image feed to the wirelessly connected device.

16. The method of claim 12, wherein after transmitting the processed ultrasound image data to the wirelessly connected device, the method further comprises:
receiving direction from the wirelessly connected device to deactivate the raw ultrasound data collection mode; and
deactivating the raw ultrasound data collection mode, such that additional raw ultrasound data is acquired for generation of additional processed ultrasound image data, without storage of the additional raw ultrasound data in the raw data buffer.

17. The method of claim 16, wherein an input indicating the raw ultrasound data collection mode of the ultrasound machine is to be activated comprises pressing of a button on a user interface provided on one of the ultrasound machine and the wirelessly connected device, and the received input indicating the raw ultrasound data collection mode of the ultrasound machine is to be deactivated comprises a release of the button.

18. A system for providing raw ultrasound data, comprising:
an ultrasound machine configured to:
acquire raw ultrasound data;
store the acquired raw ultrasound data in a raw data buffer, wherein the raw data buffer stores a first time duration of raw ultrasound data;
generate processed ultrasound image data from the raw ultrasound data, the processed ultrasound image data requiring less storage capacity than the acquired raw ultrasound data; and
transmit the processed ultrasound image data; and
a wirelessly connected device configured to:
receive processed ultrasound image data from the ultrasound machine,
store the processed ultrasound image data in an image display buffer, the image display buffer stores a second time duration of processed ultrasound image data longer than the first time duration, and wherein the image display buffer simultaneously stores: (i) the received processed ultrasound image data corresponding to and processed from the raw ultrasound data stored in the raw data buffer, and (ii) processed ultrasound image data, previously-received at the wirelessly connected device, that has no corresponding raw ultrasound data stored in the raw data buffer;

receive input selecting one or more images of the received processed ultrasound image data stored in the image display buffer, wherein (i) the received processed ultrasound image data, stored in the image display buffer, corresponding to the raw ultrasound data stored in the raw data buffer at the ultrasound machine and (ii) the previously-received processed ultrasound image data, stored in the image display buffer, that has no corresponding raw ultrasound data stored in the raw data buffer, are both viewable in a user interface of the wirelessly connected device, the user interface for navigating images stored in the image display buffer, and wherein prior to receiving input selecting the one or more images, the user interface displays an image of the processed ultrasound image data stored for the second time duration, and wherein the user interface indicates for the displayed image whether there exists to be retrieved, in the first time duration, corresponding raw ultrasound data stored in the raw data buffer in the ultrasound machine; and transmit information identifying the selected one or more images to the ultrasound machine;

wherein the ultrasound machine is further configured to:
identify the raw ultrasound data, stored in the raw data buffer, corresponding to the selected one or more images; and transmit, to the wirelessly connected device, the raw ultrasound data, stored in the raw data buffer, corresponding to the selected one or more images.

19. The method of claim 1 wherein the user interface comprises an availability indicator showing for the displayed image, whether there exists to be retrieved, in the first time duration, corresponding raw ultrasound data stored in the raw data buffer in the ultrasound machine, said availability indicator comprising a graphical element.

20. The method of claim 1 wherein the user interface comprises a data type indicator displaying type of raw ultrasound data in the raw data buffer, said type selected from the group consisting of channel domain/pre-beamformed radio frequency (RF) data, beamformed RF data, in-phase data, quadrature (IQ) data, and unprocessed B-mode data, and which are available to be retrieved.

* * * * *